(12) United States Patent
Widberg et al.

(10) Patent No.: US 12,011,013 B2
(45) Date of Patent: Jun. 18, 2024

(54) OIL BLENDS AND PROCESSES FOR THEIR PREPARATION

(71) Applicant: ENZYMOTEC LTD., Kfar Baruch (IL)

(72) Inventors: Asher Widberg, Haifa (IL); Gai Ben-Dror, Gita (IL); Maria Ilitzky Gur, Nesher (IL); Yael Herzog, Gesher HaZiv (IL)

(73) Assignee: FRUTAROM LIMITED, Migdal Haemek (IL)

( * ) Notice: Subject to any disclaimer, the term of this patent is extended or adjusted under 35 U.S.C. 154(b) by 0 days.

(21) Appl. No.: 17/534,299

(22) Filed: Nov. 23, 2021

(65) Prior Publication Data

US 2022/0079183 A1   Mar. 17, 2022

Related U.S. Application Data

(62) Division of application No. 16/310,776, filed as application No. PCT/IL2016/050894 on Aug. 17, 2016, now abandoned.

(51) Int. Cl.

| A61K 36/00 | (2006.01) |
|---|---|
| A23D 9/007 | (2006.01) |
| A23D 9/04 | (2006.01) |
| A23L 33/00 | (2016.01) |
| A23L 33/115 | (2016.01) |
| A61K 8/37 | (2006.01) |
| A61K 8/67 | (2006.01) |
| A61K 8/92 | (2006.01) |
| A61K 31/25 | (2006.01) |
| A61K 31/355 | (2006.01) |
| A61K 35/20 | (2006.01) |
| A61K 36/31 | (2006.01) |
| A61K 36/888 | (2006.01) |
| B01D 3/10 | (2006.01) |
| B01D 3/12 | (2006.01) |
| C11B 3/12 | (2006.01) |

(52) U.S. Cl.
CPC ............ *A23D 9/04* (2013.01); *A23D 9/007* (2013.01); *A23L 33/115* (2016.08); *A23L 33/40* (2016.08); *A61K 8/375* (2013.01); *A61K 8/678* (2013.01); *A61K 8/922* (2013.01); *A61K 8/925* (2013.01); *A61K 31/25* (2013.01); *A61K 31/355* (2013.01); *A61K 35/20* (2013.01); *A61K 36/31* (2013.01); *A61K 36/888* (2013.01); *B01D 3/10* (2013.01); *B01D 3/12* (2013.01); *C11B 3/12* (2013.01); *A23V 2002/00* (2013.01); *A61K 2800/5922* (2013.01)

(58) Field of Classification Search
CPC ....................................................... B01D 3/12
See application file for complete search history.

(56) References Cited

U.S. PATENT DOCUMENTS

| 4,554,107 A | 11/1985 | Takao |
| 5,230,854 A | 7/1993 | Izod et al. |
| 2008/0193624 A1 | 8/2008 | Shulman et al. |
| 2010/0021589 A1 | 1/2010 | Laskov et al. |
| 2012/0184760 A1 | 7/2012 | Saebo |
| 2012/0295009 A1 | 11/2012 | Napolitano et al. |
| 2015/0196482 A1 | 7/2015 | Bleyer et al. |
| 2017/0339971 A1 | 11/2017 | Widberg et al. |

FOREIGN PATENT DOCUMENTS

| CN | 1033191 A | 5/1989 | |
| CN | 1668631 A | 9/2005 | |
| CN | 101092359 A | 12/2007 | |
| CN | 101198261 A | 6/2008 | |
| CN | 102843921 A | 12/2012 | |
| JP | 4210437 B2 * | 1/2009 | ............... C07J 9/00 |
| JP | 2013074845 A | 4/2013 | |
| JP | 5230854 B1 | 7/2013 | |
| JP | 2015-91228 A | 5/2015 | |
| WO | 2003064444 A1 | 8/2003 | |
| WO | 2016132354 A1 | 8/2016 | |

OTHER PUBLICATIONS

Chinese Search Report in corresponding Chinese Patent Application No. 201680087333.X, dated Sep. 15, 2021, 19 pages with English Google Translation.
Chun-Yan et al., Evaluation of Oxidative Stability of Diacylglycerol and Blended Oil When Heated Up, DOI: 10.16210/i.cnki. 1007-7561.2012.02.010, Feb. 20, 2012, 4 pages with English Abstract.
Pudel et al., 3-MCPD- and glycidyl esters can be mitigated in vegetable oils by use of short path distillation, Research ARticle, Eur. J. Lipid Sci, Technol. 2016, 118, pp. 396-405.
Maduko et al., Characterization and Oxidative Stability of Structured Lipids: Infant Milk Fat Analog, Original Paper, J Am Oil Chem Soc (2008), 85, pp. 197-204.
Jin et al., Melting and Solidification Properties of Palm Kernel Oil, Tallow, and Palm Olein Blends in the Preparation of Shortening, Original Paper, J Am Oil Chem Soc (2008) 85, pp. 23-28.
Martin et al., Oxidative Stability of Structured Lipids, Review Article, Eur Food Res Technol (2010) 231, pp. 635-653.
Cermak S. et al. Distillation of Natural Fatty Acids and Their Chemical Derivatives. Distillation—Advanced from Modeling to Applications, Chapter 5, 109-140, 2012. (Year: 2012).
Skaliotis L. Short Path to Premium Quality Oils, Key No. 75171 Food Marketing & Technology Feb. 23-26, 2011. (Year: 2011).
Zarrouk A. et al. Profile of Fatty Acids, Tocopherols, Phytosterols and Polyphenols in Mediterranean Oils, Current Pharmaceutical Design 25:1971-1805, 2019. (Year: 2019).

* cited by examiner

*Primary Examiner* — Qiuwen Mi
(74) *Attorney, Agent, or Firm* — FisherBroyles, LLP; Robert Kinberg

(57) ABSTRACT

Disclosed are processes for the preparation blends of at least one oil and at least one fat and the use of such blends as ingredients of various infant formulas and other articles manufacture.

19 Claims, No Drawings

OIL BLENDS AND PROCESSES FOR THEIR PREPARATION

CROSS REFERENCE TO RELATED APPLICATIONS

This application is a Division of U.S. application Ser. No. 16/310,776, filed Dec. 17, 2018 which is a National Stage Entry of PCT/IL2016/050894, filed Aug. 17, 2016, the entire contents of which are incorporated herein by reference.

TECHNOLOGICAL FIELD

Disclosed are blends of oils and fats, processes for the preparation thereof and their use as ingredients of various infant formulas and other food articles.

REFERENCES

References considered to be relevant as background to the presently disclosed subject matter are listed below:
1. U.S. Pat. No. 4,554,107
2. US 2012/0184760

Acknowledgement of the above references herein is not to be inferred as meaning that these are in any way relevant to the patentability of the presently disclosed subject matter

TECHNOLOGICAL BACKGROUND

Molecular distillation, also known as high vacuum distillation or short path distillation, is a process of separation, purification and concentration of sensitive molecules from various compositions. The process is generally characterized by short term exposure of the composition to high temperatures, by high vacuum in the distillation column and a small distance between the evaporator and the condenser.

Molecular distillation has several advantages, for example avoiding issues of toxicity which are found in separation or purification techniques that employ solvents, minimizing losses due to thermal decomposition, and others.

Molecular distillation is suitable for purifying oils and fats from undesirable components. For example, molecular distillation is used for reducing toxins present in fish oil to levels considered to be safe, for enriching borage oil in γ-linolenic acid (GLA), for recovering tocopherols from soybean oil and for purifying diglycerides (DG) from vegetable oils and fats for a variety food applications.

Oil residues following molecular distillation processes can be used in the production of oil blends for a variety of applications in the food, cosmetics and other industries.

SUMMARY

The present inventors have surprisingly found that blends which contain residue(s) of a molecularly distilled fat(s), and also contain oil(s), exhibit greater oxidation stability when at least one of these oil(s) also underwent molecular distillation than where none of these oil(s) underwent molecular distillation. Likewise, blends which contain residue(s) of a molecularly distilled oil(s) and also contain fats(s), exhibit greater oxidation stability when at least one of these fat(s) also underwent molecular distillation than when none of these fat(s) underwent molecular distillation.

In a first aspect, the present invention provides a blend comprising at least one oil having a melting point below 15° C. and at least one fat having a melting point at or above 15° C., wherein at least one said oil and at least one said fat underwent molecular distillation, and wherein each said at least one oil is a natural oil or processed oil and each said at least one fat is a natural fat or processed fat.

In blends according to the invention, each of the at least one oil and each of the at least one fat may undergo the molecular distillation separately. Additionally and alternatively, the at least one oil and the at least one fat may be mixed together, and the resulting mixture may undergo the molecular distillation.

In blends according to the invention, the natural oil may be a vegetable oil. The processed oil in blend according to the invention may be vegetable-derived. The natural fat in blend according to the invention may be vegetable fat. The processed fat in blends according to the invention may be vegetable-derived. In some embodiments of the present invention, the fat may be milk fat, which may be natural or processed.

In blends according to the invention, the at least one oil which underwent molecular distillation may be any one of soybean oil, rapeseed oil, sunflower oil, high oleic sunflower oil, corn oil, safflower oil, MCT or high oleic safflower oil. In blends according to the invention, the at least one fat which underwent molecular distillation may be any one of palm oil, palm kernel oil, palm stearin, palm olein, coconut oil, sn-2 palmitate or milk fat.

The molecular distillation of oils and fats comprised in blends according to the invention may be performed in a distillation system under specific temperature and vacuum conditions, with the weight percentage of the at least one oil distillate resulting from the oil molecular distillation and the at least one fat distillate resulting from the fat molecular distillation being between about 2% to about 60% out of the total weight of the at least one oil and the at least one fat prior to molecular distillation thereof. The temperature of the at least one oil and/or the at least one fat under distillation may be between about 50° C. to about 400° C., and the vacuum may be between about 0.0001 mbar to about 3 mbar, the vacuum is optionally being measured at a location in the distillation system between the vacuum producing means and an external condenser. The vacuum may be between about 0.001 mbar to about 0.04 mbar, and the weight percentage of the at least one oil distillate and the at least one fat distillate resulting from the molecular distillation thereof may be between about 5% to about 45% out of the total weight of said at least one oil and at least one fat prior to said molecular distillation.

The distillation system which may be used for distilling oils and fats for the blends of the present invention may comprise an evaporator with heating media, the evaporator having an inlet position of the heating media and an outlet position of the heating media, the heating media at the inlet position being at a temperature of between about 100° C. to about 400° C.

Blends according to the invention may comprise, in addition to oil(s) and fat(s), at least one of protein(s), carbohydrate(s), mineral(s) and vitamin(s).

Blends according to the invention may exhibit a peroxide value elevation of below about 20% within 3 months storage at room temperature.

Blends according to the invention may comprise a total amount of phytosterols of less than about 4000 ppm. The endogenic tocopherol concentration in blends according to the invention may be at most 800 ppm. The weight ratio between alpha tocopherols levels to non-alpha tocopherols levels in blends according to the invention may be at least about 5. The percentage of diglycerides in blends according to the invention out of the weight of the blend may be at most about 2% w/w.

In a specific blend according to the invention, the fatty acid composition may be the following:
- 0-10% C8:0 fatty acids out of the total fatty acids;
- 0-10% C10:0 fatty acids out of the total fatty acids;
- 0-22% C12:0 fatty acids out of the total fatty acids;
- 0-15% C14:0 fatty acids out of the total fatty acids;
- 5-55% C16:0 fatty acids out of the total fatty acids;
- 1-7% C18:0 fatty acids out of the total fatty acids;
- 20-75% C18:1 fatty acids out of the total fatty acids;
- 2-40% C18:2 fatty acids out of the total fatty acids;
- 0-8% C18:3 fatty acids out of the total fatty acids; and
- other fatty acids at levels of less than 8% of the total fatty acids.

In a further aspect, the present invention provides an article of manufacture comprising at least one blend in accordance with the invention, which may be any one of a food article, a pharmaceutical preparation, a nutraceutical preparation or a cosmetic product. Specific articles of manufacture may be any one of infant formula, parenteral formula, baby food, toddler formula, child formula or adult formula, more specifically infant formulas comprising a blend according to the invention.

In an additional aspect, the present invention provides a process for the preparation of a blend comprising at least one oil having a melting point below 15° C. and at least one fat having a melting point at or above 15° C., wherein the at least one oil and the at least one fat undergo molecular distillation and wherein each of the at least one oil is a natural oil or processed oil and each of the at least one fat is a natural fat or processed fat, the process comprising the steps of:
- (i) providing at least one oil which is a natural oil or a processed oil;
- (ii) providing at least one fat which is a natural fat or a processed fat;
- (iii) (1) subjecting the at least one oil to molecular distillation in a distillation system; and
  - (2) subjecting the at least one fat to molecular distillation in a distillation system, and
  - (3) blending the residue of the at least one molecularly distilled oil obtained in step (iii)(1) with the residue of the at least one molecularly distilled fat obtained in step (iii)(2) to give a blend comprising at least one molecularly distilled oil and at least one molecularly distilled fat;
- wherein the molecular distillation is performed under specific temperature and vacuum conditions, and wherein the weight percentages of the at least one oil distillate, respectively fat distillate, resulting from the molecular distillation of the at least one oil, respectively at least one fat, may be between about 2% to about 60% out of the total weight of the oil, respectively fat, subjected to the molecular distillation;
- (iv) optionally further blending into the blend obtained in step (iii)(3) at least one additional oil which may be a natural oil or a processed oil and/or at least one additional fat which may be a natural fat or a processed fat, wherein the at least one additional oil and/or at least one additional fat may be optionally also subjected to molecular distillation under the conditions defined above prior to being blended into the blend; and
- (v) optionally blending the at least one molecularly distilled oil and at least one molecularly distilled fat obtained in step (iii)(3) or further blending the product obtained in step (iv) with any one of proteins, carbohydrates, minerals and vitamins.

In yet a further aspect, the present invention provides a process for the preparation of a blend comprising at least one oil having a melting point below 15° C. and at least one fat having a melting point at or above 15° C., wherein the at least one oil and the at least one fat undergo molecular distillation and wherein each of the at least one oil may be a natural oil or processed oil and each of the at least one fat may be a natural fat or processed fat, the process comprising the following steps:
- (i) providing at least one oil which is a natural oil or a processed oil;
- (ii) providing at least one fat which is a natural fat or a processed fat;
- (iii) (1) mixing the at least one oil with the at least one fat to give an oil and fat mixture; and
  - (2) subjecting the resulting oil and fat mixture to molecular distillation in a distillation system to give a blend comprising molecularly distilled mixture of the at least one oil and the at least one fat,
- wherein the molecular distillation may be performed under specific temperature and vacuum conditions, and wherein the weight percentage of the oil and fat mixture distillate resulting from the molecular distillation in step (iii)(2) may be between about 2% to about 60% out of the total weight of the oil and fat mixture subjected to the molecular distillation;
- (iv) optionally further blending into the resulting blend at least one additional oil which is a natural oil or a processed oil and/or at least one additional fat which is a natural fat or a processed fat, wherein the at least one additional oil and/or at least one additional fat may optionally also be subjected to molecular distillation under the conditions defined above prior to being blended into the resulting blend; and
- (v) optionally blending the at least one molecularly distilled oil and at least one molecularly distilled fat obtained in step (iii)(2) or further blending the product obtained in step (iv) with any one of proteins, carbohydrates, minerals and vitamins.

The above processes according to the present invention may be used in the preparation of any one of the oil blends of the present invention, and/or in the preparation of a lipid component of an infant formula or in the preparation of mixtures of lipid components of an infant formula.

In an additional aspect, the present invention provides method of increasing storage stability of a composition of matter that comprises at least one oil having a melting point below 15° C. or an article of manufacture comprising the composition of matter, wherein the at least one oil underwent molecular distillation before incorporation into said composition of matter, the method comprising incorporating into said composition at least one molecularly distilled fat having a melting point at or above 15° C.

In yet another one of its aspects, the invention provides a method of increasing storage stability of a composition of matter that comprises at least one fat having a melting point at or above 15° C. or an article of manufacture comprising the composition of matter, wherein the at least one fat underwent molecular distillation before incorporation into the composition of matter, the method comprising incorporating into the composition at least one molecularly distilled oil having a melting point below 15° C.

The invention of provides a storage stable article of manufacture stabilized by any of the stabilization methods according to the invention, that may be any one of a food article, a pharmaceutical preparation, a nutraceutical preparation or a cosmetic product. Specific formulas are, but not limited to, infant formulas, parenteral formulas, baby foods, toddler formulas, child formulas or adult formulas.

In order to understand the invention and to see how it may be carried out in practice, embodiments will now be described, with reference to the accompanying non-limiting examples.

DETAILED DESCRIPTION OF EMBODIMENTS

The present invention provides for the first time blends of fat(s) and oil(s), at least one of which oil(s) and at least one of which fat(s) underwent molecular distillation. The at least one fat and at least one oil can be molecularly distilled before they are blended, and their residues blended, or the said at least one oil and at least one fat can be mixed (blended) and the resulting mixture (blend) subjected to molecular distillation.

The present invention thus provides blends that comprise oil(s) (e.g., vegetable oils, natural oils, processed vegetable oils or processed oils as herein defined, or any combination of the same) and fat(s) (e.g., vegetable-derived fats, processed vegetable-derived fats or processed fats as herein defined, or any combination of the same), at least one of which oil(s) and at least one of which fat(s) underwent molecular distillation.

The term "oil" as used herein refers to an oil such as a naturally occurring oil or a processed oil, having a melting point at a temperature lower than 15° C. (room temperature) under atmospheric pressure. An oil as used herein may generally comprise substances such as but not limited to triglycerides, diglycerides, monoglycerides, free fatty acids and some other substances such as phospholipids, sterols, sterol esters, stanols, stanol esters, tocopherols and other vitamins.

The term "fat" as used herein refers to an oil such as a naturally occurring oil or a processed oil, having a melting point at a temperature at or above 15° C. A fat as used herein may generally comprise substances such as but not limited to triglycerides, diglycerides, monoglycerides, free fatty acids and some other substances such as phospholipids, sterols, sterol esters, stanols, stanol esters, tocopherols and other vitamins.

"About" as used herein generally refers to approximate values. When referred to a dose of cannabinoids in milligrams, "about" should be understood as including the range of a value ±15%. When referred to other values, the term should be understood as including the range of a value ±15%, for example ±15%, ±12%, ±10%, ±8%, ±5%, ±2% or ±1%.

As used here in the term "oil(s)" refers to one oil ("oil") and/or two oils or more ("oils"). The term "fat(s)" as used herein refers to one fat ("fat") and/or two fats or more ("fats").

As used herein, the terms "blend" or "oil blend" or "oil and fat blend" refers to a blend of at least one oil having a melting point at a temperature lower than 15° C., and at least one fat, having a melting point at a temperature at or above 15° C., in which at least one said oil and at least one said fat underwent molecular distillation. The oil(s) and/or fat(s) can be each separately molecularly distilled before being incorporated (blended) into the blend. Alternatively, the oil(s) and/or fat(s) can be mixed, then molecularly distilled, and subsequently incorporated (blended) into the blend. Mixing can be of more than one oil, of more than one fat, or of one oil and one fat, or of more than one oil with one fat, or of more than one oil with more than one fat, or of more than one fat with one oil. The term "oil blend" or "oil and fat blend" as used herein is also to be taken to mean a composition essentially comprised of oil blends as herein defined. It is noted that the oil blends may generally comprise substances such as but not limited to triglycerides, diglycerides, monoglycerides, free fatty acids and some other substances such as phospholipids and tocopherols.

As used herein, the terms "processed oil" and "processed fat" refer to oil, respectively fat, as herein defined, which underwent any possible type of process including, but not limited to, a reaction between two or more triglycerides, a reaction between triglycerides and free fatty acids, fractionation and hydrogenation. Non limiting examples of processed oils are Medium Chain Triglyceride (MCT) oil and sn2-palmitate oil.

As used herein the term "MCT oil" refers to an oil which is mainly in the triglyceride form and containing mainly capric (C8:0) and caprylic (C10:0) fatty acids. The MCT oil may be prepared by an esterification process between glycerol and fatty acids in their free, methyl ester or ethyl ester form.

As used herein the terms "sn2-palmitate", "beta-palmitate", "OPO" and "β-palmitate" are interchangeable and refer to structured triglycerides in which the percentage (level) of palmitic acid moieties at the sn-2 position of the glycerol backbone is at least 33% of the total palmitic acid. The sn2-palmitate may be prepared, for example, by an enzymatic reaction between fatty acid donors (optionally free fatty acids, methyl esters or ethyl esters) containing mainly unsaturated fatty acids and triglycerides containing mainly saturated fatty acids. Preferably both fatty acid donors and triglycerides are derived from vegetable source.

As used herein the term "mainly" is to be understood as constituting at least 50% of the specified feature.

As used herein, the term "vegetable oil" refers to an oil from vegetable sources. The vegetable oil may be a natural vegetable oil or a processed oil from vegetable source.

As used herein, the term "vegetable fat" refers to a fat from vegetable sources. The vegetable fat may be a natural vegetable fat or a processed fat from vegetable source.

As used herein the term "milk fat" refers to fat from mammalian milk sources. At times, "milk fat" refers to fat from bovine milk source. The milk fat may be natural milk fat or a processed milk fat.

As used herein the term "vegetable oil blend" refers to a blend of one or more vegetable oils as herein defined and one or more vegetable fats as herein defined, of which at least one oil and at least one fat underwent molecular distillation before being blended or after being mixed and the mixture distilled to form the vegetable oil blend or being incorporated (blended) into the blend. Each of the vegetable oils and each of the vegetable fats in the vegetable oil blend may be either natural vegetable oil, respectively fat, or processed oil, respectively fat, from vegetable source. The term "vegetable oil blend" as used herein is also to be taken to mean a composition essentially comprised of vegetable oil blends as herein defined. It is noted that vegetable oils such as natural vegetable oil or fat or processed oil or fat from vegetable source may generally comprise substances such as but not limited to triglycerides, diglycerides, monoglycerides, free fatty acids and some other substances such as phospholipids and tocopherols.

As used herein the term "processed oil from vegetable source" refers to an oil as herein defined which underwent any process step provided that most of the triglyceride molecules in said processed oil are essentially the same as those originated from the vegetable source or were produced in a reaction between two or more triglycerides (e.g. interesterification or transesterification of a single vegetable oil or between two or more vegetable oils).

As used herein the term "processed fat from vegetable source" refers to a fat as herein defined which underwent any process step provided that most of the triglyceride molecules in said processed fat are essentially the same as those originated from the vegetable source or were produced in a reaction between two or more triglycerides (e.g. interesterification or transesterification of a single vegetable fat or between two or more vegetable fats).

As used herein, the at least one fat or processed fat comprised in the "blend" or "oil blend" or "oil and fat blend" as defined herein can be milk fat, respectively processed milk fat.

The terms "molecularly distilled oil" and "molecularly distilled fat" as used herein refer to an oil, respectively fat, that underwent molecular distillation.

Further provided is a blend comprising at least one oil having a melting point below 15° C., and at least one fat having a melting point at or above 15° C., wherein at least one said oil is a molecularly distilled oil and at least one said fat is a molecularly distilled fat, and wherein each said at least one oil is a natural oil or processed oil and each said at least one fat is a natural fat or processed fat.

In a further of its aspects the present invention provides oil blends as herein disclosed wherein the oil blends have an endogenic tocopherol (TCP) concentration of at most about 800 ppm.

As used herein, the term "endogenous tocopherol concentration" refers to tocopherol levels which are present in the oil source without the external addition of natural or synthetic tocopherols.

In some embodiments the oil blends (e.g., vegetable oil blends, vegetable oil blends comprising milk fat) according to the invention have endogenic tocopherol concentration below about 600 ppm, at times below about 500 ppm or 400 ppm, at times below about 300 ppm, even at times below about 200 ppm, even at times, below about 100 ppm, at times below about 50 ppm, at times below about 30 ppm, at times below about 20 ppm, even at times below about 10 ppm.

In some embodiments the ratio (w/w) between alpha tocopherols levels to non-alpha tocopherols levels in the oil blends (e.g., vegetable oil blends) according to the invention is at least about 5. At times said ratio is about 8 or above, at times about 10 or above, at times about 15 or above, at times about 20 or above, even at times about 10 to about 20.

In some embodiments the oil blends (e.g., vegetable oil blends) according to the invention contain total amount of phytosterols of less than about 4000, at times of less than about 3000 or 2000 ppm, preferably less than about 1500 or 1000 ppm, more preferably less than about 800 or 600 ppm, even more preferably less than about 400 or 300 ppm and most preferably less than about 200 or 100 ppm.

As used herein the terms "phytosterol content", "total amount of phytosterols" or any lingual variations thereof are interchangeable and are to be envisaged as the sum of free phytosterols, free phytostanols, esterified phytosterols, esterified phytostanols and any other derivatives or forms of plant source sterol or stanol in their free form equivalent (e.g. for esters, their non-esterified form).

As used herein, the terms "esterified phytosterols", "esterified phytostanols", "phytosterol esters", "phytostanol esters", "fatty acid phytosterol esters", "fatty acid phytostanol esters" or any lingual variations thereof are interchangeable. The concentration of these esters or esterified species is measured in their free form (i.e., not esterified) equivalents.

As used herein, the term "free form equivalent" refers to the phytosterol component within the phytosterol or phytostanol esters which is in its free form and not in the esterified form.

As used herein the terms "fatty acid phytosterol esters" and "fatty acid phytostanol esters" refers to phytosterol or phytostanol esterified with a fatty acid residue, respectively.

In some embodiments the percentage of diglyceride level (w/w) out of the oil blends (e.g., vegetable oil blends) according to the invention is at most about 2%, at times said percentage is about 1.5% or below, at times about 1% or below, at times about 0.5% or below. At times said percentage is about 0.3% or below, at times about 0.2% or below, at times about 0.1% or below, at times about 0.05% or below, even at times about 0.01% or below.

In another one of its aspects the present invention provides nutritional compositions, pharmaceutical compositions, nutraceutical compositions, parenteral nutrition compositions, functional food or medical food comprising an oil blend (e.g., vegetable oil blend) according to the invention for use in preparations for enteral or parenteral administration to a subject. Such preparations may be referred to as enteral or parenteral preparations.

A nutritional composition as used herein may be any nutritional composition including, but not limited to: human milk fat substitute, parenteral formula composition, infant formula, adult formula, dairy product, milk powder, drinks, ice cream, biscuit, soy product, bakery, pastry, bread, cake, sauce, soup, prepared food, frozen food, condiment, confectionary, oil, fat, margarine, spread, filling, cereal, instant product, infant food, toddler food, bar, snack, candy, and chocolate product.

The term "infant formula" as used herein refers to an edible product of manufacture, designed for feeding infants (as herein defined). The product serves, generally, as a human milk substitute, but although sometime considered to be essentially a mimetic of human milk, it differs from human milk. An infant formula comprises fat(s), carbohydrates(s), protein(s), vitamin(s), mineral(s), essential elements, etc. When in dry form (powder form), the product can be diluted with liquids, generally water, and fed to infants, to supply nutritional requirements. Oil blends in accordance with the present invention can be used as the fat ingredient, or major or partial fat ingredient of infant formulas.

The term "adult formula" as used herein refers to an edible product of manufacture, designed for feeding adults, usually adults with specific nutritional requirements. An adult formula comprises fat(s), carbohydrates(s), protein(s), vitamin(s), mineral(s), essential elements, etc., to supply nutritional needs. When in dry form (powder form), the composition of matter can be diluted with liquids, for example water or nutritional liquids such a milk, fed to adults. Oil blends in accordance with the present invention can be used as the fat ingredient, or major or partial fat ingredient of adult nutritional formulas.

A functional food as used herein can be any functional food, including, but not limited to: dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy, and chocolate product. Generally, functional foods have a potential positive effect on health or wellbeing of the consumer, beyond that of ordinary food or standard nutrition.

A nutraceutical composition as used herein can be any nutraceutical, which can be any substance that may be considered as a food or part of a food and provides medical or health benefits, including the prevention and treatment of diseases or disorders. Such nutraceutical compositions include, but are not limited to: a food additive, a food supplement, a dietary supplement, genetically engineered foods (such as for example vegetables, herbal products, and processed foods such as cereals, soups, and beverages), stimulant functional food, medical food, parenteral nutrition, and pharmafood (also sometimes designated "phood"). Dietary supplements may be delivered in the form of soft gel capsules, tablets, syrups, and other known dietary supplement delivery systems.

The pharmaceutical or nutraceutical compositions may be in any of the many dosage delivery forms commonly used in the art. Pharmaceutical compositions suitable for oral administration may be presented as discrete dosage units (such as pills, tablets, pellets, dragées, capsules, or softgel capsules), as a powder or granule, or as a liquid form, for example solution, suspension, syrup, or elixir. Solutions/suspensions may be formulated for intravenous administration.

A medical food as used herein is specially formulated and intended for the dietary management of a disease/disorder that has distinctive nutritional needs that cannot be met by normal diet alone.

In another of its aspects the present invention provides a formula, an infant formula, parenteral formula, baby food, toddler formula, child formula or adult formula comprising any one of the oil blends (e.g., vegetable oil blends) according to the present invention.

The oil blends (e.g., vegetable oil blends) according to the present invention may be comprised within nutritional compositions, pharmaceutical compositions, nutraceutical compositions, parenteral nutrition compositions, functional foods or medical foods.

The oil blends (e.g., vegetable oil blends) according to the present invention may be comprised within an infant formula, at times within a parenteral formula, at times within baby food, at times within toddler formula, at times within a child formula, even at times within an adult formula.

In some embodiments the ratio (w/w) between alpha tocopherols levels to non-alpha tocopherols levels in a formula of the invention is at least about 5. At times said ratio is about 8 or above, at times about 10 or above, at times about 15 or above, at times about 20 or above and at times about 10 to about 20.

In some embodiments the weight percentage of diglycerides (w/w) in the oil blend (e.g., vegetable oil blend) of the invention in a formula (e.g., an infant formula) according to the invention is at most 2%, at times said percentage is about 1.5% or below, at times about 1% or below, at times about 0.5% or below. At times said percentage is about 0.3% or below, at times about 0.2% or below, at times about 0.1% or below, at times about 0.05% or below and at times about 0.01% or below.

As used herein the terms "parenteral formula" and "parenteral nutrition composition" or any lingual variations thereof are envisaged as being applicable for administration to a subject body via a route different from the digestive system and may supply part or all of the daily nutritional requirements. Non limiting examples of such administration are via intravenous, total parenteral nutrition (TPN), partial parenteral nutrition, total nutrient admixture (TNA), partial nutrient admixture, peripheral parenteral nutrition (PPN) routes, etc. Other parenteral routes of administration may be intramuscular, intraperitoneal, subcutaneous administrations, etc. Specific examples of parenteral formulas are infant parenteral formulas and adult parenteral formulas.

In some embodiments the oil blend according to the invention can further comprise at least one structured triglyceride, preferably enriched with palmitic acid at the sn-2 position of the triglyceride.

In some embodiments the vegetable oil blend according to the invention can further comprise at least one of MCT oil and sn2-palmitate oil.

In some embodiments the oil blends according to the invention may comprise at least one oil, at least two oils, at least three oils, at least four oils, at least five oils, at least six oils, at least seven oils, at least eight oils, at least nine oils, at least ten oils, at least eleven oils, at least twelve oils, at least thirteen oils, at least fourteen oils etc., and/or at least one fat, at least two fats, at least three fats, at least four fats, at least five fats, at least six fats, at least seven fats, at least eight fats, at least nine fats, at least ten fats, at least eleven fats, at least twelve fats, at least thirteen fats, at least fourteen fats etc. The oils and/or fats may be vegetable oils, respectively fats, natural oils, respectively fats, processed oils, respectively fats, from vegetable source, or processed oils, respectively fats, as herein defined. The at least one fat comprised in the blends of the present invention can also be milk fat or processed milk fat.

In some embodiments the oil blends according to the invention can comprise or contain at least one, at times at least two, at times at least three, at times at least four at times at least five, at times at least six, at times at least seven and at times all eight of the following oils: soybean oil, rapeseed oil, sunflower oil, high oleic sunflower oil, corn oil, safflower oil, MCT or high oleic safflower oil; and at least one, at times at least two, at times at least three, at times at least four, at times at least five, at times at least six and at times all seven of the following fats: palm oil, palm kernel oil, palm stearin, palm olein, coconut oil, sn2-palmitate or milk fat.

As used herein the term "rapeseed oil" encompasses also canola oil.

In some embodiments the oil blends according to the invention comprise or contain at least one, at times at least two, at times at least three, at times at least four and even at times, at least five of the following oils: soybean oil, rapeseed oil, sunflower oil, high oleic sunflower oil, corn oil, safflower oil or high oleic safflower oil; and at least one, at times at least two, at times and at least three of the following fats: palm oil, palm kernel oil, palm stearin, palm olein, coconut oil, sn-2 palmitate or milk fat.

In some embodiments the oil blends according to the invention may comprise or contain, but not limited to, one of the following oils and fats combinations: coconut oil, soybean oil, high oleic sunflower oil and palm oil; or, coconut oil, soybean oil and high oleic safflower oil; or, palm kernel oil, rapeseed oil, sunflower oil, high oleic sunflower oil and palm oil; or, palm kernel oil, rapeseed oil and sunflower oil; or, palm kernel oil, soybean oil, rapeseed oil, sunflower oil and palm oil; coconut oil, soybean oil and palm oil; or, palm kernel oil, soybean oil, rapeseed oil and sunflower oil; or, palm kernel oil, soybean oil, rapeseed oil, sunflower oil and high oleic sunflower oil; or, coconut oil, rapeseed oil, sunflower oil and high oleic sunflower oil; or, palm kernel oil, rapeseed oil, sunflower oil or, high oleic sunflower oil; coconut oil, rapeseed oil and sunflower oil.

In some embodiments the oil blends according to the invention comprise OPO (sn2-palmitate), palm kernel oil, rapeseed oil and sunflower oil. In some embodiments the OPO percentage (w/w) out of the total oils is 1%-90%, at times 5%-70%, at times 10%-60, at times 20%-50%, even at times 30%-40%; the palm kernel oil percentage (w/w) out of the total oils is 1%-90%, at times 5%-70%, at times 7%-50%, at times 10%-40%, at times 15%-30%, even at times 20%-25%; the rapeseed oil percentage (w/w) out of the total oils is 1%-90%, at times 5%-70%, at times 7%-50%, at times 10%-40%, even at times, 15%-30%; the sunflower oil percentage (w/w) out of the total oils is 1%-90%, at times 3%-70%, at times 5%-40, even at times, 10%-20%.

In some embodiments the oil blends according to the invention comprise coconut oil, soybean oil, high oleic sunflower oil and palm oil. In some embodiments the coconut oil percentage (w/w) out of the total oils is 1%-90%, at times 5%-70%, at times 7%-50%, at times 10%-40%, at times 15%-30%, even at times, 20%-25%; the soybean oil percentage (w/w) out of the total oils is 1%-90%, at times 5%-70%, at times 7%-50%, at times 10%-40%, at times 15%-30%, even at times, 20%-25%; the high oleic sunflower oil percentage (w/w) out of the total oils is 1%-90%, at times 3%-70%, at times 5%-40, even at times, 10%-20%; the palm oil percentage (w/w) out of the total oils is 1%-90%, at times 10%-70%, at times 20%-60%, at times 30%-50%, even at times, 40%-45%.

In some embodiments the oil blends according to the invention comprise coconut oil, soybean oil and high oleic safflower oil. In some embodiments the coconut oil percentage (w/w) out of the total oils is 1%-90%, at times 5%-70%, at times 10%-50%, at times 20%-40%, even at times 25%-35%; the soybean oil percentage (w/w) out of the total oils is 1%-90%, at times 5%-70%, at times 10%-50%, at times 20%-40%, even at times 25%-35%; the high oleic safflower oil percentage (w/w) out of the total oils is 1%-90%, at times 5%-70%, at times 10%-60%, at times 20%-50%, even at times, 30%-45%.

In some embodiments the oil blends according to the invention comprise palm kernel oil, soybean oil, high oleic sunflower oil and palm oil. In some embodiments the palm kernel oil percentage (w/w) out of the total oils is 1%-90%, at times 5%-70%, at times 10%-50%, even at times, 20%-30%; the soybean oil percentage (w/w) out of the total oils is 1%-90%, at times 3%-50%, even at times 10%-20%; the high oleic sunflower oil percentage (w/w) out of the total oils is 1%-90%, at times 3%-50%, even at times, 10%-20%; the palm oil percentage (w/w) out of the total oils is 1%-90%, at times 5%-70%, at times 10%-60%, at times 20%-50%, even at times, 30%-45%.

The following is accepted nomenclature of several saturated fatty acids: caprylic acid (octanoic acid, C8:0), capric acid (decanoic acid, C10:0), lauric acid (dodecanoic acid, C12:0), myristic acid (tetradecanoic acid, C14:0), palmitic acid (hexadecanoic acid, C16:0), stearic acid (octadecanoic acid, C18:0).

The following is accepted nomenclature of several unsaturated fatty acid: oleic acid (C18:1), linoleic acid (C18:2), α-linolenic acid (C18:3), arachidonic acid (C20:4), eicosapentaenoic acid (EPA) (C20:5), docosapentaenoic acid (DPA) (C22:5) and docosahexaenoic acid (DHA) (C22:6).

In some embodiments the fatty acid composition of the oil blend according to the invention is as follows:
  0-10% C8:0 fatty acids out of the total fatty acids;
  0-10% C10:0 fatty acids out of the total fatty acids;
  0-22% C12:0 fatty acids out of the total fatty acids;
  0-15% C14:0 fatty acids out of the total fatty acids;
  5-55% C16:0 fatty acids out of the total fatty acids;
  1-7% C18:0 fatty acids out of the total fatty acids;
  20-75% C18:1 fatty acids out of the total fatty acids;
  2-40% C18:2 fatty acids out of the total fatty acids;
  0-8% C18:3 fatty acids out of the total fatty acids; and
  other fatty acids present in levels of less than 8% of the total fatty acids.

In an additional aspect, the present invention provides a process for the preparation of a blend comprising at least one oil having a melting point below 15° C. and at least one fat having a melting point at or above 15° C., wherein the at least one oil and the at least one fat undergo molecular distillation and wherein each of the at least one oil is a natural oil or processed oil and each of the at least one fat is a natural fat or processed fat, the process comprising the steps of:
  (i) providing at least one oil which is a natural oil or a processed oil;
  (ii) providing at least one fat which is a natural fat or a processed fat;
  (iii) (1) subjecting the at least one oil to molecular distillation in a distillation system; and
    (2) subjecting the at least one fat to molecular distillation in a distillation system, and
    (3) blending the residue of the at least one molecularly distilled oil obtained in step (iii)(1) with the residue of the at least one molecularly distilled fat obtained in step (iii)(2) to give a blend comprising at least one molecularly distilled oil and at least one molecularly distilled fat;
  wherein the molecular distillation is performed under specific temperature and vacuum conditions, and wherein the weight percentages of the at least one oil distillate, respectively fat distillate, resulting from the molecular distillation of the at least one oil, respectively at least one fat, may be between about 2% to about 60% out of the total weight of the oil, respectively fat, subjected to the molecular distillation;
  (iv) optionally further blending into the blend obtained in step (iii)(3) at least one additional oil which may be a natural oil or a processed oil and/or at least one additional fat which may be a natural fat or a processed fat, wherein the at least one additional oil and/or at least one additional fat may be optionally also subjected to molecular distillation under the conditions defined above prior to being blended into the blend; and
  (v) optionally blending the at least one molecularly distilled oil and at least one molecularly distilled fat obtained in step (iii)(3) or further blending the product obtained in step (iv) with any one of proteins, carbohydrates, minerals and vitamins.

In the above process according to the invention, the weight percentage of the oil distillate resulting from the molecular distillation of the at least one oil may be at least about 15% out of the total weight of the oil and the fat distillate resulting from the molecular distillation of the at least one fat may be between about 3% to about 40% out of the total weight of the fat subjected to the molecular distillation.

In a further aspect, the present invention provides a process for the preparation of a blend comprising at least one oil having a melting point below 15° C. and at least one fat having a melting point at or above 15° C., wherein the at least one oil and the at least one fat undergo molecular distillation and wherein each of the at least one oil may be a natural oil or processed oil and each of the at least one fat may be a natural fat or processed fat, the process comprising the following steps:
- (i) providing at least one oil which is a natural oil or a processed oil;
- (ii) providing at least one fat which is a natural fat or a processed fat;
- (iii) (1) mixing the at least one oil with the at least one fat to give an oil and fat mixture; and
  - (2) subjecting the resulting oil and fat mixture to molecular distillation in a distillation system to give a blend comprising molecularly distilled mixture of the at least one oil and the at least one fat, wherein the molecular distillation may be performed under specific temperature and vacuum conditions, and wherein the weight percentage of the oil and fat mixture distillate resulting from the molecular distillation in step (iii)(2) may be between about 2% to about 60% out of the total weight of the oil and fat mixture subjected to the molecular distillation;
- (iv) optionally further blending into the resulting blend at least one additional oil which is a natural oil or a processed oil and/or at least one additional fat which is a natural fat or a processed fat, wherein the at least one additional oil and/or at least one additional fat may optionally also be subjected to molecular distillation under the conditions defined above prior to being blended into the resulting blend; and
- (v) optionally blending the at least one molecularly distilled oil and at least one molecularly distilled fat obtained in step (iii)(2) or further blending the product obtained in step (iv) with any one of proteins, carbohydrates, minerals and vitamins.

In the above processes, the distillation system may comprise vacuum generating means and at least one internal condenser; the temperature of the oil(s) or fat(s) or mixture of oil(s) and fat(s) under distillation may be between about 50° C. to about 400° C.; and the vacuum may be between about 0.0001 mbar to about 3 mbar, as measured optionally at a location in the system between vacuum producing means and an external condenser. Further, the distillation system may comprise an evaporator with heating medium, the evaporator having an inlet position and an outlet position, where the heating medium at the inlet position may be at a temperature of between about 100° C. to about 400° C. The temperature of the internal condenser may be at most about 90° C. The vacuum may be at most of about 2 mbar.

In the above processes the oils may be any one of soybean oil, rapeseed oil, sunflower oil, high oleic sunflower oil, corn oil, safflower oil, MCT or high oleic safflower oil. The fats may be any one of palm oil, palm kernel oil, palm stearin, palm olein, coconut oil, sn2-palmitate or milk fat.

According to a specific embodiment the at least one oil is any one of rapeseed oil, soybean oil or sunflower oil and the weight percentage of the oil or oils distillate resulting from molecular distillation thereof is at least about 15% out of the total weight of the oil or oils subjected to said molecular distillation and the at least one fat is any one of palm kernel oil or coconut oil wherein the weight percentage of the fat or fats distillate resulting from molecular distillation thereof is between about 3% to about 40% out of the total weight of the fat or fats subjected to said molecular distillation.

The above processes according to the present invention may be used in the preparation of any one of the oil blends of the present invention, and/or in the preparation of a lipid component of an infant formula or in the preparation of mixtures of lipid components of an infant formula.

According to some embodiments the molecular distillation is performed in a distillation system under specific temperature and vacuum conditions, and wherein the weight percentage of the oil distillate, or fat distillate or mixed oil and fat distillate resulting from the molecular distillation thereof is between about 2% to about 60% out of the total weight of the oil, fat or oil and fat mixture, respectively, subjected to the molecular distillation.

The weight percentage of oils and fats that underwent molecular distillation comprised in blends in accordance with the present invention out of the total blend weight can be more than 20% w/w, at times more than 25% w/w, at times more than 30% w/w, at time more than 35% w/w, at times more than 40% w/w, at times more than 45% w/w, at times more than 50% w/w, at time more than 55% w/w, at times more than 60% w/w, at times more than 65% w/w, at time more than 70% w/w, at times more than 75% w/w, at times more than 80% w/w, at time more than 85% w/w, at time more than 90% w/w and at times up to 100% w/w out of the total weight of the blend.

The weight ratio of oils that underwent molecular distillation (distilled oils) and fats that underwent molecular distillation (distilled fats) comprised in blends in accordance with the present invention can be from about 10%/90%, at times about 20%/80%, at times about 30%/70%, at times about 40%/60%, at times about 50%/50%, at times about 60%/40%, at times about 70%/30%, at times about 80%/20% and up to about 90%/10% oil/fat.

According to some embodiments the molecular distillation is performed in a distillation system, wherein the system comprises vacuum generating means and at least one internal condenser and optionally at least one external condenser, wherein the temperature of the oil(s) under distillation or fat(s) under distillation or mixed oil(s) and fat(s) under distillation is between about 50° C. to about 400° C. and the vacuum is between about 0.0001 mbar to about 3 mbar, the vacuum optionally being measured at a location in the system between vacuum producing means (e.g., a vacuum pump) and the external condenser and wherein the weight percentage of the oil(s) distillate, or fat distillate(s) or mixed oil(s) and fat(s) distillate resulting from the molecular distillation thereof is between about 2% to about 60% out of the total weight of the oil, fat or oil and fat mixture, respectively, subjected to the molecular distillation.

In some embodiments the distillation system comprises an evaporator with heating media (e.g., steam, thermal oil and the like), the evaporator having an inlet position of the heating media and an outlet position of the heating media, wherein the heating media being at a temperature of at least about 190° C. at the inlet position, at times about 210° C. or above, at times about 220° C. or above, at times about 230° C. or above, at times about 260° C. and above, even at times about 300° C. and above. In some embodiments the heating media is at a temperature of between about 100° C. to about 400° C., at times between about 150° C. to about 360° C., at times between about 300° C. to about 360° C., at times between about 200° C. to about 350° C., and at times between about 200° C. to about 300° C.

In some embodiments the temperature of the oil(s) or fat(s) or oil(s) and fat(s) mixtures under distillation is between about 100° C. to about 350° C., at times between about 200° C. to about 300° C., at times between about 100° C. to about 200° C., at times between about 150° C. to about 200° C. and at times between about 150° C. to about 190° C.

In some embodiments the distillation system comprises an internal condenser. In some embodiments the internal condenser's temperature is at most of about 90° C. At times said temperature is about 70° C. or below, at times about 60° C. or below, at times about 50° C. or below, at times about 40° C. or below, and at times the internal condenser temperature is between 60° C. to 80° C.

In some embodiments the distillation system comprises an external condenser. In some embodiments the external condenser's temperature is above −80° C. and below 0° C. At times said temperature is above −60° C. and below 0° C., at times above −40° C. and below 0° C., at times above −40° C. and below −10° C., at times above −30° C. and below −10° C. and at times about −20° C.

In some embodiments the vacuum is at most of about 2 mbar. In some embodiments the vacuum is about 1 mbar or below, at times about 0.5 mbar or below, at times of about 0.1 mbar or below, at times about 0.05 mbar or below, at times 0.03 mbar or below, at times 0.02 mbar or below, at times about 0.01 mbar or below, at times 0.005 mbar or below, at times 0.001 mbar or below and at times 0.0005 mbar or below.

In some embodiments the weight percentage of the oil(s) distillate, or fat(s) distillate or mixed oil(s) and fat(s) distillate resulting from the molecular distillation thereof is between about 2% to about 50% out of the total weight of the oil(s), fat(s) or oil(s) and fat(s) mixture, respectively, subjected to the molecular distillation at times between about 5% to about 45%, at times between about 10% to about 40% and at times between 20% to about 40%. At times weight percentage of the oil(s) distillate, or fat(s) distillate or mixed oil(s) and fat(s) distillate resulting from the molecular distillation thereof is at least about 2%, at times above 5% and at times above 9%, 17%, 25%, 35% or 50% out of the total weight of the oil(s), fat(s) or oil(s) and fat(s) mixture, respectively, subjected to the molecular distillation.

In some embodiments the weight percentage of the oil(s) distillate or fat(s) distillate or oil(s) and fat(s) mixture distillate resulting from the molecular distillation thereof is between about 5% to about 40%. At times the weight percentage of the oil(s) distillate or fat(s) distillate or oil(s) and fat(s) mixture distillate resulting from the molecular distillation thereof is between 6% to 35%, at times between 6% to 30%, at times between about 6% to about 20% and at times between about 10% to about 20% out of the total weight of the oil(s) or fat(s) or oil(s) and fat(s) mixture subjected to the molecular distillation.

In some embodiments the oil or oils (e.g., at least one oil, at least two oils, at least one other oil and at least one further oil) may be any one of rapeseed oil, soybean oil or sunflower oil, high oleic sunflower oil, corn oil, safflower oil, MCT or high oleic safflower oil and the weight percentage of the oil or oils distillate resulting from the molecular distillation thereof is at least about 15% out of the total weight of the oil or oils subjected to the molecular distillation. At times said weight percentage is above about 17%, at times above about 25%, at times above about 35% and at times above about 40% out of the total weight of the oil or oils subjected to the molecular distillation.

In some embodiments the fat or fats (e.g., at least one fat, at least two fats, at least one other fat and at least one further fat) may be any one of palm oil, palm kernel oil, palm stearin, palm olein, coconut oil, sn2-palmitate or milk fat, and the weight percentage of the fat or fats distillate resulting from the molecular distillation thereof is between about 3% to about 40% out of the total weight of the oil or oils subjected to the molecular distillation. At times said weight percentage is between about 5% to about 30%, at times between about 6% to about 30%, at times between about 6% to about 20% and at times between about 10% to about 20% out of the total weight of the oil or oils subjected to the molecular distillation.

As shown in the following examples, blends according to the invention exhibit are more stable and resistant to oxidation, as measured by peroxide value (PV) after three weeks incubation at room temperature, compared to other blends. As shown in Example 2 (Table 3) a blend in accordance with the invention which contained fat residue resulting from molecular distillation of palm oil, blended with a residue of molecularly distilled rapeseed oil was substantially more stable, exhibiting no change in PV from baseline, than a blend of the same residue of molecularly distilled palm oil with non-distilled rapeseed oil, which exhibited a 30% increase in PV. Surprisingly, the same blend of palm oil residue with rapeseed oil residue (no change in PV) was also more stable than a blend of palm oil residue blended with palm kernel oil residue (20% increment in PV).

Example 3 (Table 4), also shows that blends in accordance with the invention are more stable and resistant to oxidation, as measured by peroxide value after one week incubation at accelerated conditions of 40° C., compared to other blends. The results demonstrate again that blends which contain an oil residue resulting from molecular distillation of rapeseed oil, blended with a residue of molecularly distilled fat (palm kernel oil residue and palm oil residue) were more stable (no change in PV residue) than blends of the same rapeseed oil residue with non-distilled fats (palm kernel oil, 16% increase in PV and palm oil residue 220% increase of PV, respectively).

The present invention thus provides oil blends that are storage stable and are resistant to oxidation, in which the elevation in peroxide value within storage at room temperature for at least 3 months is below 20% compared to the base value (time zero). For example, the elevation in peroxide value of blends in accordance with the invention following storage at room temperature for at least three months, can be lower than 19%, 18%, 17%, 16%, 15%, 14%, 13%, 12%, 11%, 10%, 9%, 8%, 7%, 6%, 5%, 4%, 3%, 2%, 1,% and even no elevation (zero elevation). For example, some specific blends in accordance with the invention exhibit no elevation at all of peroxide value after storage at room temperature for three weeks, and even no change in peroxide value after one week at accelerated conditions of 40° C., from baseline initial peroxide value. These blend all comprise at least one oil and at least one fat that underwent molecular distillation. Articles of manufacture, such as, but not limited to food articles, pharmaceutical preparations, nutraceutical preparations or cosmetic products comprising the fat blends of the invention will also possess the same storage stability. Specific articles of manufacture are, for example, but no limited to, infant formulas, parenteral formulas, baby foods, toddler formulas, child formulas or adult formulas.

Based on the findings presented in the present examples, as discussed in detail above, in a further aspect the present invention provides a method of increasing storage stability or reducing susceptibility to oxidation thereby increasing storage stability of a composition of matter that comprises at least one oil having a melting point below 15° C., or an article of manufacture comprising said composition of matter, wherein said at least one oil underwent molecular distillation before incorporation into said composition of matter, said method comprising incorporating into said composition at least one molecularly distilled fat having a melting point at or above 15° C. Similarly, the present invention provides a method of increasing storage stability of a composition of matter that comprises at least one fat having a melting point at or above 15° C., or an article of manufacture comprising said composition of matter, wherein said at least one fat underwent molecular distillation before incorporation into said composition of matter, said method comprising incorporating into said composition at least one molecularly distilled oil having a melting point below 15° C. The article of manufacture comprising the composition of matter with increased storage stability and resistance to oxidation can be any one of a food article, a pharmaceutical preparation, a nutraceutical preparation or a cosmetic product. Specific articles of manufactures are, for example, but not limited to infant formula, parenteral formula, baby food, toddler formula, child formula or adult formula.

In a specific embodiment, the present invention provides an infant formula comprising an oil blend in accordance with the invention. Such infant formula may further comprises any or several of fat(s), carbohydrates(s), protein(s), vitamin(s), mineral(s) and essential elements.

In a further aspect, the present invention provides the oil blends as herein disclosed for use as lipid ingredients in formulas such as infant formula.

In a further aspect the present invention provides the oil blends as herein disclosed for use as lipid ingredients in nutritional compositions, pharmaceutical compositions, nutraceutical compositions, parenteral nutrition composition, functional food or medical food.

In a further aspect the present invention provides the oil blends as herein disclosed for use in the preparation of nutritional compositions, pharmaceutical compositions, nutraceutical compositions, parenteral nutrition composition, functional food or medical food.

In another aspect the present invention provides a composition comprising an oil blend (e.g., vegetable oil blend) according to the invention for use in enteral or parenteral preparations for administration to a subject.

In another aspect the present invention provides nutritional compositions, pharmaceutical compositions, nutraceutical compositions, parenteral nutrition compositions, functional food or medical food comprising an oil blend (e.g., vegetable oil blend) according to the invention for use in enteral or parenteral preparations for administration to a subject.

In another aspect the present invention provides an infant formula, parenteral formula, baby food, toddler formula, child formula or adult formula comprising the oil blend (e.g., vegetable oil blend) according to the invention for use in enteral or parenteral preparations for administration to a subject.

In another aspect the present invention provides a method of reducing and/or optimizing phytosterol levels in a subject, the method comprises administering to the subject an oil blend according to the invention.

In another aspect the present invention provides an oil blend according to the invention for (or being used for, or being used in a method for) reducing and/or optimizing phytosterol levels in a subject.

In some embodiments the reduction and/or optimization are of the subject's phytosterol plasma level.

In another aspect the present invention provides a method of reducing phytosterolemia in a subject, the method comprises administering to the subject the oil blend according to the invention.

In yet another aspect the present invention provides an oil blend according to the invention for (or being used for, or being used in a method for) reducing phytosterolemia in a subject.

In another aspect the present invention provides a method of reducing the risk and/or severity of parenteral nutrition-associated liver disease (PNALD) in a subject, the method comprises administering to the subject the oil blend according to the invention.

In yet another aspect the present invention provides an oil blend according to the invention for (or being used for, or being used in a method for) reducing the risk and/or severity of parenteral nutrition-associated liver disease (PNALD) in a subject.

In another aspect the present invention provides a method of reducing the risk and/or severity of parenteral nutrition-associated cholestasis (PNAC) in a subject, the method comprises administering to the subject the oil blend according to the invention.

In yet another aspect the present invention provides an oil blend according to the invention for (or being used for, or being used in a method for) reducing the risk and/or severity of parenteral nutrition-associated cholestasis (PNAC) in a subject.

In another aspect the present invention provides a method of reducing and/or optimizing bilirubin levels in a subject, the method comprises administering to the subject the oil blend according to the invention.

In yet another aspect the present invention provides an oil blend according to the invention for (or being used for, or being used in a method for) reducing and/or optimizing bilirubin levels in a subject.

In some embodiments reduced and/or optimized bilirubin levels are bilirubin plasma levels.

In another aspect the present invention provides method for enhancing and/or optimizing absorption of fat and/or fat soluble nutrients and/or fat soluble vitamins in a subject, the method comprises administering the oil blend (e.g., vegetable oil blend) according to the invention to the subject.

In yet another aspect the present invention provides an oil blend according to the invention for (or being used for, or being used in a method for) enhancing and/or optimizing absorption of fat and/or fat soluble nutrients and/or fat soluble vitamins is a subject.

Fat soluble nutrients comprise but not limited to vitamin A, D, E or K, ascorbyl palmitate, carotenoids, carotene, lutein, zeaxanthin, lycopene, hormones and steroids.

In another aspect the present invention provides method for increasing and/or optimizing dietary energy potential in a subject, the method comprises administering the oil blend (e.g., vegetable oil blend) according to the invention to the subject.

In yet another aspect the present invention provides an oil blend according to the invention for (or being used for, or being used in a method for) increasing and/or optimizing dietary energy potential in a subject.

In another aspect the present invention provides method for increasing and/or optimizing one or more of cholesterol, HDL cholesterol, VLDL and LDL cholesterol levels (e.g., plasma levels, levels in the liver etc.) in a subject, the method comprises administering the oil blend (e.g., vegetable oil blend) according to the invention to the subject.

In yet another aspect the present invention provides an oil blend according to the invention for (or being used for, or being used in a method for) increasing and/or optimizing one or more of cholesterol, HDL cholesterol, VLDL and LDL cholesterol levels (e.g., plasma levels, levels in the liver etc.) in a subject.

In another aspect the present invention provides method for optimizing one or more of LDL particles size, triglyceride levels, Apolipoprotein A levels and Apolipoprotein B levels (e.g., in the plasma or the liver) in a subject, the method comprises administering the oil blend (e.g., vegetable oil blend) according to the invention to the subject.

In yet another aspect the present invention provides an oil blend according to the invention for (or being used for, or being used in a method for) optimizing one or more of LDL particles size, triglyceride levels, Apolipoprotein A levels and Apolipoprotein B levels (e.g., in the plasma or the liver) in a subject.

In another one of its aspects the present invention provides method for increasing and/or optimizing bile acid secretion in a subject, the method comprises administering the oil blend (e.g., vegetable oil blend) according to the invention to the subject.

In yet another one of its aspects the present invention provides an oil blend according to the invention for (or being used for, or being used in a method for) increasing and/or optimizing bile acid secretion in a subject.

In another one of its aspects the present invention provides method for controlling and/or optimizing bile acid levels (e.g. plasma levels) in a subject, the method comprises administering the oil blend (e.g., vegetable oil blend) according to the invention to the subject.

In yet another one of its aspects the present invention provides an oil blend according to the invention for (or being used for, or being used in a method for) controlling and/or optimizing bile acid levels (e.g. plasma levels) in a subject.

In another one of its aspects the present invention provides method for reducing and/or optimizing endogenous cholesterol synthesis in a subject, the method comprises administering the oil blend (e.g., vegetable oil blend) according to the invention to the subject.

In yet another one of its aspects the present invention provides an oil blend according to the invention for (or being used for, or being used in a method for) reducing and/or optimizing endogenous cholesterol synthesis in a subject.

In another one of its aspects the present invention provides method for optimizing and/or enhancing carotenoids absorption in a subject, the method comprises administering the oil blend (e.g., vegetable oil blend) according to the invention to the subject.

In yet another one of its aspects the present invention provides an oil blend according to the invention for (or being used for, or being used in a method for) enhancing and/or optimizing carotenoids absorption in a subject.

In another one of its aspects the present invention provides method for promoting and/or enhancing beneficial gut flora in a subject, the method comprises administering the oil blend (e.g., vegetable oil blend) according to the invention to the subject.

In yet another one of its aspects the present invention provides an oil blend according to the invention for (or being used for, or being used in a method for) promoting and/or enhancing beneficial gut flora in a subject.

In some embodiments the oil blend according to the invention is effective to promote development of gut flora comprising predominantly bifidobacteria and lactobacilli.

In another one of its aspects the present invention provides method for preventing at least one of phytosterolemia, cardiovascular diseases, hypercholesterolemia, hypertriglyceridemia, diabetes, metabolic syndrome and atherosclerosis in a subject, the method comprises administering the oil blend (e.g., vegetable oil blend) according to the invention to a subject.

In yet another one of its aspects the present invention provides an oil blend according to the invention for (or being used for, or being used in a method for) preventing at least one of phytosterolemia, cardiovascular diseases, hypercholesterolemia, hypertriglyceridemia, diabetes, metabolic syndrome and atherosclerosis in a subject.

In another one of its aspects the present invention provides method for reducing inflammation and/or CRP levels in a subject, the method comprises administering the oil blend (e.g., vegetable oil blend) according to the invention to the subject.

In yet another one of its aspects the present invention provides an oil blend according to the invention for (or being used for, or being used in a method for) reducing inflammation and/or CRP levels in a subject.

In another one of its aspects the present invention provides method for reducing and/or optimizing glucose and/or insulin levels in a subject, the method comprises administering the oil blend (e.g., vegetable oil blend) according to the invention to the subject.

In yet another one of its aspects the present invention provides an oil blend according to the invention for (or being used for, or being used in a method for) reducing and/or optimizing glucose and/or insulin levels in a subject.

In some embodiments according to the present invention each and any one of reducing and/or optimizing phytosterol levels; reducing phytosterolemia; reducing the risk and/or severity of PNALD; reducing the risk and/or severity of PNAC; reducing and/or optimizing bilirubin levels; enhancing and/or optimizing absorption of fat and/or fat soluble nutrients and/or fat soluble vitamins; increasing and/or optimizing dietary energy potential; increasing and/or optimizing one or more of cholesterol, HDL cholesterol, VLDL and LDL cholesterol levels (e.g., plasma levels, levels in the liver etc.); optimizing one or more of LDL particles size, triglyceride levels, Apolipoprotein A levels and Apolipoprotein B levels; increasing and/or optimizing bile acid secretion; controlling and/or optimizing bile acid levels (e.g. plasma levels); reducing and/or optimizing endogenous cholesterol synthesis; optimizing and/or enhancing carotenoids absorption; promoting and/or enhancing beneficial gut flora; preventing at least one of phytosterolemia, cardiovascular diseases, hypercholesterolemia, hypertriglyceridemia, diabetes, metabolic syndrome and atherosclerosis; reducing inflammation and/or CRP levels; or reducing and/or optimizing glucose and/or insulin levels, is in comparison with the subject baseline parameters.

The term "level" herein and throughout also includes "plasma level" and "tissue level" of a subject.

In some embodiments according to the present invention each and any one of reducing and/or optimizing phytosterol levels; reducing phytosterolemia; reducing the risk and/or severity of PNALD; reducing the risk and/or severity of PNAC; reducing and/or optimizing bilirubin levels; enhancing and/or optimizing absorption of fat and/or fat soluble nutrients and/or fat soluble vitamins; increasing and/or optimizing dietary energy potential; increasing and/or optimizing one or more of cholesterol, HDL cholesterol, VLDL and LDL cholesterol levels (e.g., plasma levels, levels in the liver etc.); optimizing one or more of LDL particles size, triglyceride levels, Apolipoprotein A levels and Apolipoprotein B levels; increasing and/or optimizing bile acid secretion; controlling and/or optimizing bile acid levels (e.g. plasma levels); reducing and/or optimizing endogenous cholesterol synthesis; optimizing and/or enhancing carotenoids absorption; promoting and/or enhancing beneficial gut flora; preventing at least one of phytosterolemia, cardiovascular diseases, hypercholesterolemia, hypertriglyceridemia, diabetes, metabolic syndrome and atherosclerosis; reducing inflammation and/or CRP levels; or reducing and/or optimizing glucose and/or insulin levels, is in comparison with the relevant parameter levels when a subject is administered with a conventional oil blend i.e., an oil blend in which less than two oils underwent molecular distillation.

In some embodiments the nutritional compositions, pharmaceutical compositions, nutraceutical compositions, parenteral nutrition compositions, functional food, medical food or formulas, including infant formulas, according to the invention (comprising the oil blends according to the invention) may be useful in each and any one of reducing phytosterolemia; reducing the risk and/or severity of PNALD; reducing the risk and/or severity of PNAC; reducing and/or optimizing bilirubin levels; enhancing and/or optimizing absorption of fat and/or fat soluble nutrients and/or fat soluble vitamins; increasing and/or optimizing dietary energy potential; increasing and/or optimizing one or more of cholesterol, HDL cholesterol, VLDL and LDL cholesterol levels (e.g., plasma levels, levels in the liver etc.); optimizing one or more of LDL particles size, triglyceride levels, Apolipoprotein A levels and Apolipoprotein B levels; increasing and/or optimizing bile acid secretion; controlling and/or optimizing bile acid levels (e.g. plasma levels); reducing and/or optimizing endogenous cholesterol synthesis; optimizing and/or enhancing carotenoids absorption; promoting and/or enhancing beneficial gut flora; preventing at least one of phytosterolemia, cardiovascular diseases, hypercholesterolemia, hypertriglyceridemia, diabetes, metabolic syndrome and atherosclerosis; reducing inflammation and/or CRP levels; or reducing and/or optimizing glucose and/or insulin levels.

As used herein, the term "subject" refers to a healthy subject or a subject suffering from a specific disorder (a non-healthy subject) or a subject at risk of developing a specific disorder. The subject may be a child including an infant and a toddler and an adult including a male, a female, a teenager, an elderly senior subject and a geriatric subject.

Optionally, in all aspects and embodiments of the present disclosure, the subject may be under parenteral nutrition or under partial parenteral nutrition, or a subject that cannot tolerate enteral feeding or a subject that requires non enteral feeding.

Further, the term "child" includes infants (from day of birth, newborn, to about 12 months i.e., about 1 year) as well as toddlers (from about one year up to about the age of 3).

An "infant" as used herein is meant to encompass a human infant, including but not limited to, a newborn, a very early preterm infant, a preterm infant, a term infant, a small for gestation infant and a small premature infants.

The term "newborn" includes pre-mature infants, post-mature infants and full term newborns.

In some non-limiting embodiments the subject may suffer from one or more of reduced intestinal absorption, reduced gastrointestinal function, prematurity, intestinal inflammation, celiac disease, malabsorption related to different diseases, intestinal failure, short bowel syndrome, intestinal failure secondary to short bowel syndrome, congenital absorption defects, necrotizing enterocolitis, intestinal malformations, gastrointestinal fistulas, bowel obstruction, severe acute pancreatitis, cystic fibrosis, compromised intestinal function, Crohn's disease, cancer, a condition that result from low blood flow to the bowels, conditions which relate to and/or result from parenteral nutrition.

DESCRIPTION OF NON-LIMITING EXAMPLES

Example 1: Reducing Diglycerides Levels Vegetable Oils Using Molecular Distillation 2000 gr rapeseed oil, palm oil and palm kernel oil (Florin-Netherland) containing 0.49% (w/w), 6.13% (w/w) and 0.61% (w/w) diglycerides, respectively, were processed using a pilot scale molecular distillation unit (VK 125-15, VTA company, Germany) with an evaporator having an inlet position and an outlet position. First the oils were fed (each separately) into a heated feed vessel at 50° C. and then pumped into a wiped film evaporator (degassing stage) to remove water and air residues (4.7-5 mbar and 145-185° C.). From the degassing stage the oil was pumped using a feed rate of about 12 kg/hr into the short path distillation unit with the evaporator having an inlet position and an outlet position. Distillation parameters are summarized in Table 1.

TABLE 1

Distillation parameters

| | Inlet temp. of evaporator heating media (° C.) | Oil temp. * (° C.) | Pressure (mbar) | Internal Condenser temp. (° C.) | w/w % distillate out of total oil subjected to distillation |
|---|---|---|---|---|---|
| Rapeseed oil 483-42 | 314 | 285 | 0.013 | 70 | 40 |
| Palm oil 483-44 | 296.6 | 268 | 0.0133 | 70 | 30 |
| Palm kernel oil 483-43 | 236.4 | 220 | 0.012 | 70 | 20 |

* estimated

Residue fraction and distillate fraction were collected. The weight percentage of the distillate resulting from the molecular distillation was calculated out of the initial amount and is presented in Table 1.

As shown in Table 2 the molecular distillation resulted in oil and fat residues with significantly reduced diglycerides (DG) content compared the DG in the oil before distillation.

The stability of the above mentioned individual distilled oils and fats is significantly lower in comparison with the corresponding non-distilled oil or fat.

TABLE 2

Diglyceride (DG) content of oil residues following molecular distillation

| | Rapeseed oil residue 483-42-17 | Palm Kernel oil residue 483-43-11 | Palm oil residue 483-44-11 |
|---|---|---|---|
| DG content (% w/w) residue | <0.01 | 0.19 | 0.75 |

Example 2: Stability of Molecularly Distilled Fat (Palm Oil) and Non-Distilled Oil Blend VS Molecularly Distilled Fat and Molecularly Distilled Oil Blend Three aliquots, each of 30 gr of palm oil residue following molecular distillation (Example 1), were mixed each with one of the following oils (as described in Example 1):
1. 30 gr rapeseed oil (Florin—Netherland)
2. 30 gr rapeseed oil residue following molecular distillation (483-42-17)
3. 30 gr of palm kernel oil residue following molecular distillation (483-43-11)

Stability of all three blends was tested at baseline (t=0), and following incubation at room temperature for 3 weeks, using peroxide value (PV) measurements. The results of the stability test are summarized in Table 3 and demonstrate that a blend which contains a fat residue resulting from molecular distillation (palm oil residue) blended with a residue of molecularly distilled oil (rapeseed oil) is substantially more stable (no change in PV) than when blended with a non-distilled rapeseed oil (30% increase in PV). Surprisingly, the palm oil residue blended with rapeseed oil residue (no change in PV) was also more stable than a blend of palm oil (a fat) residue blended with palm kernel oil residue (20% increment in PV).

TABLE 3

PV change of oil blends containing palm oil residue and another oil/fat following 3 weeks at room temperature

| Blending oil/fat | Rapeseed oil (483-49-8) | Rapeseed oil residue after molecular distillation (483-49-2) | Palm kernel oil residue after molecular distillation (483-49-6) |
|---|---|---|---|
| PV (% Change from Baseline) | 30 | 0 | 20 |

Example 3: Stability of Different Blends Containing Rapeseed Oil Residue Following Molecular Distillation Four aliquots, each of 30 gr of rapeseed oil residue following molecular distillation (Example 1), were mixed each with one of the following oils (as described in Example 1):
1. 30 gr palm kernel oil (Florin-Netherland)
2. 30 gr palm kernel oil residue following molecular distillation (483-43-11)
3. 30 gr of palm oil (Florin-Netherland)
4. 30 gr of palm oil residue following molecular distillation (483-44-11)

Stability of all four blends was tested at baseline (t=0), following one week incubation at accelerated conditions of 40° C. using peroxide value (PV) measurements. The results of the stability test are summarized in Table 4 and demonstrate again that blends (483-49-1 and 483-49-2) which contain an oil residue resulting from molecular distillation (rapeseed oil residue) blended with a residue of molecularly distilled fat (palm kernel oil residue and palm oil residue, respectively) were more stable (no change in PV residue) than blends (483-49-9 and 483-49-11) of the rapeseed oil residue with non-distilled fats (palm kernel oil, 16% increase in PV and palm oil residue, 220% increase of PV, respectively).

TABLE 4

PV change in blends containing rapeseed oil residue and a blending fat following 1 week at accelerated conditions of 40° C.

| Blending fat | Palm kernel oil (483-49-9) | Palm kernel oil residue after molecular distillation (483-49-1) | Palm oil (483-49-11) | Palm oil residue after molecular distillation (483-49-2) |
|---|---|---|---|---|
| PV (% Change from Baseline) | 16 | 0 | 220 | 0 |

The invention claimed is:

1. A process for the preparation of a blend comprising at least one oil having a melting point below 15° C. and at least one fat having a melting point at or above 15° C., said process comprising:
   (i) providing the at least one oil which is a natural oil or a processed oil;
   (ii) providing the at least one fat which is a natural fat or a processed fat;
   (iii) molecularly distilling said at least one oil in a distillation system to form a first distillation residue; and
   (iv) molecularly distilling said at least one fat in a distillation system to form a second distillation residue, and
   (v) blending the first distillation residue with the second distillation residue to form a blend thereof;
      wherein said distillation system comprises vacuum generating means and at least one internal condenser;
      the temperature of the oil(s) or fat(s) or mixture of oil(s) and fat(s) under distillation is between about 50° C. to about 400° C.; and
      wherein the vacuum is between about 0.0001 mbar to about 3 mbar, said vacuum being measured at a location in said system between vacuum producing means and an external condenser.

2. The process according to claim 1, further comprising blending into the blend at least one additional oil and/or at least one additional fat, wherein said at least one additional oil and/or at least one additional fat is also subjected to molecular distillation.

3. The process according to claim 1, further comprising adding any one of fats, oils, proteins, carbohydrates, minerals, and vitamins to the blend.

4. The process according to claim 1, wherein the weight percentage of the first distillate residue is at least about 15% out of the total weight of said at least one oil and the second distillate residue is between about 3% to about 40% out of the total weight of said at least one fat.

5. A process according to claim 1, wherein said distillation system comprises an evaporator with heating medium, said evaporator having an inlet position and an outlet position, the heating medium at the inlet position being at a temperature of between about 100° C. to about 400° C.

6. A process according to claim 1, wherein the temperature of the internal condenser is at most about 90° C.

7. The process according to claim 1, wherein the vacuum is at most of about 2 mbar.

8. The process according to claim 1, wherein said at least one oil is any one of soybean oil, rapeseed oil, canola oil, sunflower oil, high oleic sunflower oil, corn oil, safflower oil, MCT or high oleic safflower oil and said fat is any one of palm oil, palm kernel oil, palm stearin, palm olein, coconut oil, sn2-palmitate, or milk fat.

9. The process according to claim 1, wherein said at least one oil is rapeseed oil or canola oil and said at least one fat is palm oil or palm kernel oil.

10. The process according to claim 1, wherein said blend is suitable for constituting a lipid component of an infant formula, parenteral formula, baby food, toddler formula, child formula, or adult formula.

11. A process according to claim 1, wherein said blend is comprised in a composition of matter or in an article of manufacture comprising said composition of matter, wherein said article of manufacture is any one of infant formula, parenteral formula, baby food, toddler formula, child formula or adult formula, wherein the storage stability of said composition of matter or of said article of manufacture is increased compared to the storage stability of a composition of matter or article of manufacture comprising said composition of matter that contain a blend of an oil and a fat that did not undergo said molecular distilling.

12. The process according to claim 1, wherein the weight percentages of the at least one oil distillate resulting from said molecular distillation of said at least one oil and the weight percentages of the at least one fat distillate resulting from said molecular distillation of said at least fat, is each between about 2% to about 60% out of the total weight of the oil and fat subjected to said molecular distillation.

13. The process according to claim 1, wherein said at least one oil is any one of rapeseed oil or canola oil, and wherein the weight percentage of the oil or oils distillate resulting from molecular distillation thereof is at least about 15% out of the total weight of the oil or oils subjected to said molecular distillation and wherein said at least one fat is any one of palm oil or palm kernel oil and wherein the weight percentage of the fat or fats distillate resulting from molecular distillation thereof is between about 3% to about 40% out of the total weight of the fat or fats subjected to said molecular distillation.

14. The process according to claim 1, wherein the blend has a peroxide value elevation within 3 months storage at room temperature that is below 20%.

15. The process according to claim 1, wherein the blend has a total amount of phytosterols that is less than about 4000 ppm.

16. The process according to claim 1, wherein the fatty acid composition in said blend is the following:
   0-10% C8:0 fatty acids out of the total fatty acids;
   0-10% C10:0 fatty acids out of the total fatty acids;
   0-22% C12:0 fatty acids out of the total fatty acids;
   0-15% C14:0 fatty acids out of the total fatty acids;
   5-55% C16:0 fatty acids out of the total fatty acids;
   1-7% C18:0 fatty acids out of the total fatty acids;
   20-75% C18:1 fatty acids out of the total fatty acids;
   2-40% C18:2 fatty acids out of the total fatty acids;
   0-8% C18:3 fatty acids out of the total fatty acids; and
   other fatty acids at levels of less than 8% of the total fatty acids.

17. The process according to claim 1, wherein the blend has an endogenic tocopherol concentration that is at most 800 ppm.

18. The process according to claim 1, wherein the blend has a weight ratio between alpha tocopherols levels to non-alpha tocopherols levels that is at least about 5.

19. A process for the preparation of a blend comprising at least one oil having a melting point below 15° C. and at least one fat having a melting point at or above 15° C., said process comprising:
   (i) providing the at least one oil which is a natural oil or a processed oil;
   (ii) providing the at least one fat which is a natural fat or a processed fat;
   (iii) molecularly distilling said at least one oil in a distillation system to form a first distillation residue; and
   (iv) molecularly distilling said at least one fat in a distillation system to form a second distillation residue, and
   (v) blending the first distillation residue with the second distillation residue to form a blend thereof;
   wherein the blend has an endogenic tocopherol concentration that is at most 800 ppm.

* * * * *